(12) United States Patent
Jackson

(10) Patent No.: US 10,561,444 B2
(45) Date of Patent: Feb. 18, 2020

(54) PIVOTAL BONE ANCHOR ASSEMBLY WITH TWIST-IN-PLACE INSERT HAVING RADIALLY OFFSET RECEIVER ENGAGING STRUCTURES

(71) Applicant: Roger P. Jackson, Prairie Village, KS (US)

(72) Inventor: Roger P. Jackson, Prairie Village, KS (US)

( * ) Notice: Subject to any disclaimer, the term of this patent is extended or adjusted under 35 U.S.C. 154(b) by 0 days.

(21) Appl. No.: 16/411,826

(22) Filed: May 14, 2019

(65) Prior Publication Data

US 2019/0274736 A1 Sep. 12, 2019

Related U.S. Application Data

(63) Continuation of application No. 15/940,343, filed on Mar. 29, 2018, now Pat. No. 10,335,200, which is a continuation-in-part of application No. 15/389,296, filed on Dec. 22, 2016, now abandoned, which is a continuation of application No. 12/661,042, filed on Mar. 10, 2010, now abandoned, and a continuation-in-part of application No. 12/229,207, filed on Aug. 20, 2008, now Pat. No. 8,353,932.

(60) Provisional application No. 61/210,058, filed on Mar. 13, 2009, provisional application No. 60/994,083, filed on Sep. 17, 2007.

(51) Int. Cl.
*A61B 17/70* (2006.01)

(52) U.S. Cl.
CPC ........ *A61B 17/7031* (2013.01); *A61B 17/701* (2013.01); *A61B 17/702* (2013.01); *A61B 17/7008* (2013.01); *A61B 17/7022* (2013.01); *A61B 17/7029* (2013.01); *A61B 17/7035* (2013.01); *A61B 17/7037* (2013.01); *A61B 17/7032* (2013.01); *Y10T 29/49826* (2015.01)

(58) Field of Classification Search
CPC ............ A61B 17/7034; A61B 17/7037; A61B 17/701

See application file for complete search history.

(56) References Cited

U.S. PATENT DOCUMENTS

| | | | |
|---|---|---|---|
| 4,805,602 A | 2/1989 | Puno et al. | |
| 4,946,458 A | 8/1990 | Harms et al. | |
| 5,129,388 A | 7/1992 | Vignaud et al. | |
| 5,167,664 A | 12/1992 | Hodorek | |
| 5,207,678 A | 5/1993 | Harms et al. | |

(Continued)

*Primary Examiner* — Ellen C Hammond
(74) *Attorney, Agent, or Firm* — Polsinelli PC

(57) ABSTRACT

A pivotal bone anchor assembly includes a shank, a receiver with an open channel in communication with an axial bore, and a pressure insert with an upwardly-facing seating surface for receiving an elongate rod. The axial bore includes a downwardly-facing surface below a closure top mating feature and one or more integral structures protruding inwardly toward a central longitudinal axis. The insert includes one or more notches formed into an outer side surface and an upwardly-facing surface positioned radially outward from the seating surface. Upon installation into the axial bore, the insert is rotatable about the longitudinal axis until the insert upwardly-facing surface is rotated under the receiver downwardly-facing surface to inhibit upward movement of the insert within the axial bore along the longitudinal axis and the receiver inwardly-protruding structures become positioned within the insert outer notches to prevent further rotation of the insert within the axial bore.

26 Claims, 6 Drawing Sheets

(56) References Cited

U.S. PATENT DOCUMENTS

| | | |
|---|---|---|
| 5,261,912 A | 11/1993 | Frigg |
| 5,312,404 A | 5/1994 | Asher et al. |
| 5,360,431 A | 11/1994 | Puno et al. |
| 5,395,371 A | 3/1995 | Miller et al. |
| 5,429,639 A | 7/1995 | Judet |
| 5,443,467 A | 8/1995 | Biedermann et al. |
| 5,466,237 A | 11/1995 | Byrd, III et al. |
| 5,474,555 A | 12/1995 | Puno et al. |
| 5,476,462 A | 12/1995 | Allard et al. |
| 5,476,464 A | 12/1995 | Metz-Stavenhagen et al. |
| 5,496,321 A | 3/1996 | Puno et al. |
| 5,554,157 A | 9/1996 | Errico et al. |
| 5,569,247 A | 10/1996 | Morrison |
| 5,584,834 A | 12/1996 | Errico et al. |
| 5,586,984 A | 12/1996 | Errico et al. |
| 5,591,166 A | 1/1997 | Bernhardt et al. |
| 5,601,553 A | 2/1997 | Trebing et al. |
| 5,607,426 A | 3/1997 | Ralph et al. |
| 5,624,442 A | 4/1997 | Mellinger et al. |
| 5,669,911 A | 9/1997 | Errico et al. |
| 5,672,176 A | 9/1997 | Biedermann et al. |
| 5,681,319 A | 10/1997 | Biedermann et al. |
| 5,690,630 A | 11/1997 | Errico et al. |
| 5,716,356 A | 2/1998 | Biedermann et al. |
| 5,725,528 A | 3/1998 | Errico et al. |
| 5,728,098 A | 3/1998 | Sherman et al. |
| 5,733,286 A | 3/1998 | Errico et al. |
| 5,738,685 A | 4/1998 | Halm et al. |
| 5,782,833 A | 7/1998 | Haider |
| 5,797,911 A | 8/1998 | Sherman et al. |
| 5,800,435 A | 9/1998 | Errico et al. |
| 5,817,094 A | 10/1998 | Errico et al. |
| 5,863,293 A | 1/1999 | Richelsoph |
| 5,873,878 A | 2/1999 | Harms et al. |
| 5,876,402 A | 3/1999 | Errico et al. |
| 5,879,350 A | 3/1999 | Sherman et al. |
| 5,879,351 A | 3/1999 | Viart |
| 5,882,350 A | 3/1999 | Ralph et al. |
| 5,885,286 A | 3/1999 | Sherman et al. |
| 5,891,145 A | 4/1999 | Morrison et al. |
| 5,954,725 A | 9/1999 | Sherman et al. |
| 5,961,517 A | 10/1999 | Biedermann et al. |
| 5,964,760 A | 10/1999 | Richelsoph |
| 6,010,503 A | 1/2000 | Richelsoph et al. |
| 6,019,759 A | 2/2000 | Rogozinski |
| 6,022,350 A | 2/2000 | Ganem |
| 6,053,917 A | 4/2000 | Sherman et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,086,588 A | 7/2000 | Ameil et al. |
| 6,090,110 A | 7/2000 | Metz-Stavenhagen |
| 6,090,111 A | 7/2000 | Nichols |
| 6,099,528 A | 8/2000 | Saurat |
| 6,110,172 A | 8/2000 | Jackson |
| 6,113,601 A | 9/2000 | Tatar |
| 6,132,431 A | 10/2000 | Nilsson et al. |
| 6,132,432 A | 10/2000 | Richelsoph |
| 6,132,434 A | 10/2000 | Sherman et al. |
| 6,146,383 A | 11/2000 | Studer et al. |
| 6,187,005 B1 | 2/2001 | Brace et al. |
| RE37,161 E | 5/2001 | Michelson et al. |
| 6,224,596 B1 | 5/2001 | Jackson |
| 6,248,105 B1 | 6/2001 | Schlapfer et al. |
| 6,254,602 B1 | 7/2001 | Justis |
| 6,273,888 B1 | 8/2001 | Justis |
| 6,280,442 B1 | 8/2001 | Barker et al. |
| 6,280,445 B1 | 8/2001 | Morrison et al. |
| 6,287,308 B1 | 9/2001 | Betz et al. |
| 6,287,311 B1 | 9/2001 | Sherman et al. |
| 6,302,888 B1 | 10/2001 | Mellinger et al. |
| 6,309,391 B1 | 10/2001 | Crandall et al. |
| 6,355,040 B1 | 3/2002 | Richelsoph et al. |
| RE37,665 E | 4/2002 | Ralph et al. |
| 6,368,321 B1 | 4/2002 | Jackson |
| 6,440,137 B1 | 8/2002 | Horvath et al. |
| 6,443,953 B1 | 9/2002 | Perra et al. |
| 6,471,705 B1 | 10/2002 | Biedermann et al. |
| 6,485,494 B1 | 11/2002 | Haider |
| 6,488,681 B2 | 12/2002 | Martin et al. |
| 6,520,963 B1 | 2/2003 | McKinley |
| 6,554,834 B1 | 4/2003 | Crozet et al. |
| 6,565,565 B1 | 5/2003 | Yuan et al. |
| 6,565,567 B1 | 5/2003 | Haider |
| 6,626,908 B2 | 9/2003 | Cooper et al. |
| 6,652,526 B1 | 11/2003 | Arafiles |
| 6,660,004 B2 | 12/2003 | Barker et al. |
| 6,695,843 B2 | 2/2004 | Biedermann et al. |
| 6,716,214 B1 | 4/2004 | Jackson |
| 6,755,829 B1 | 6/2004 | Bono et al. |
| 6,835,196 B2 | 12/2004 | Biedermann et al. |
| 6,837,889 B2 | 1/2005 | Shluzas |
| 6,840,940 B2 | 1/2005 | Ralph et al. |
| 7,066,937 B2 | 6/2006 | Shluzas |
| 7,087,057 B2 | 8/2006 | Konieczynski |
| 7,160,300 B2 | 1/2007 | Jackson |
| 7,306,606 B2 | 12/2007 | Sasing |
| 7,503,924 B2 | 3/2009 | Lee |
| 7,678,137 B2 | 3/2010 | Butler et al. |
| 7,717,939 B2 | 5/2010 | Ludwig et al. |
| 9,788,866 B2 | 10/2017 | Jackson |
| 2001/0001119 A1 | 5/2001 | Lombardo |
| 2003/0100896 A1 | 5/2003 | Biedermann et al. |
| 2003/0149431 A1 | 8/2003 | Varieur |
| 2003/0187433 A1 | 10/2003 | Lin |
| 2004/0153068 A1 | 8/2004 | Janowski et al. |
| 2004/0193160 A1 | 9/2004 | Richelsoph |
| 2004/0225289 A1 | 11/2004 | Biedermann et al. |
| 2004/0236330 A1 | 11/2004 | Purcell et al. |
| 2004/0267264 A1 | 12/2004 | Konieczynski et al. |
| 2005/0049589 A1 | 3/2005 | Jackson |
| 2005/0080420 A1 | 4/2005 | Farris et al. |
| 2005/0192573 A1 | 9/2005 | Abdelgany et al. |
| 2006/0129149 A1 | 6/2006 | Iott et al. |
| 2006/0217716 A1 | 9/2006 | Baker et al. |
| 2006/0264933 A1 | 11/2006 | Baker et al. |
| 2006/0276789 A1 | 12/2006 | Jackson |
| 2007/0270813 A1 | 11/2007 | Garamszegi |
| 2010/0036433 A1 | 2/2010 | Jackson |

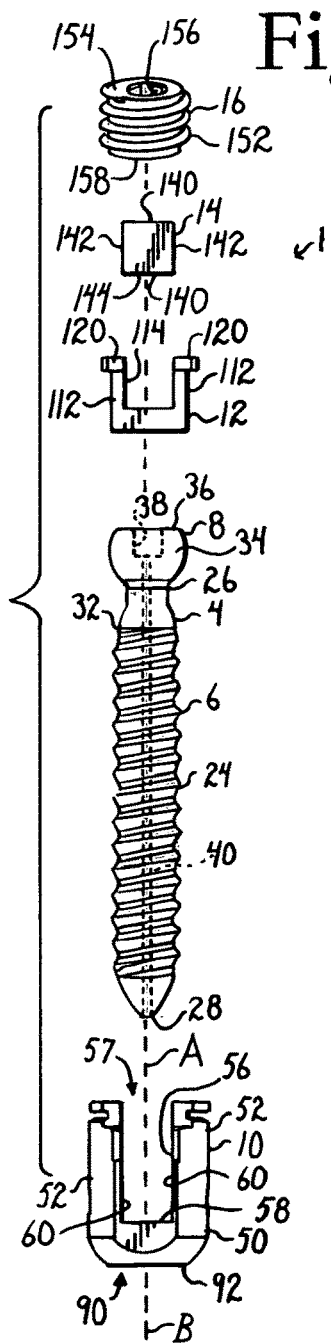
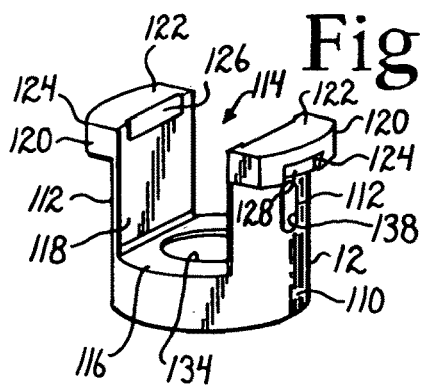
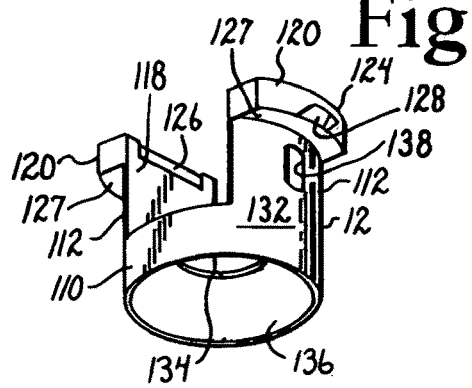
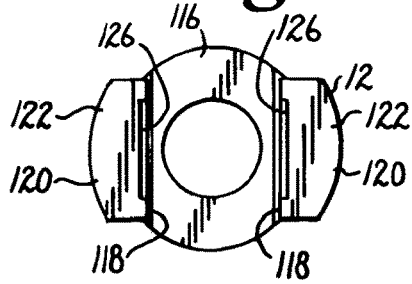
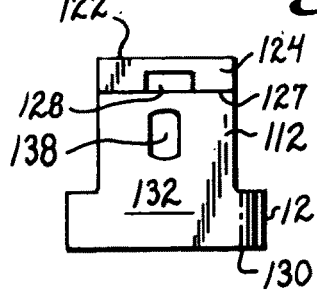

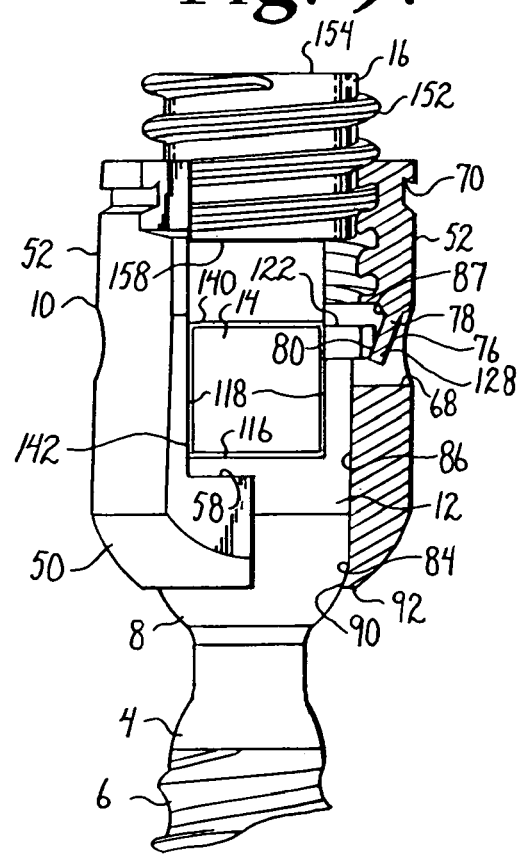
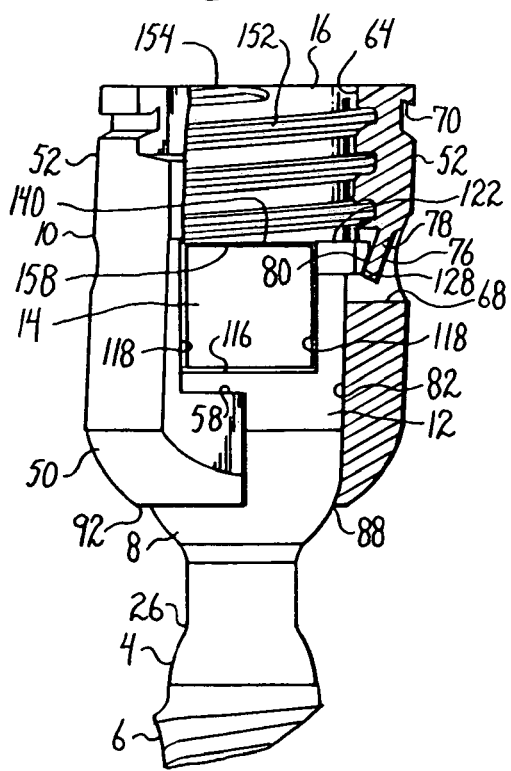

PIVOTAL BONE ANCHOR ASSEMBLY WITH TWIST-IN-PLACE INSERT HAVING RADIALLY OFFSET RECEIVER ENGAGING STRUCTURES

CROSS-REFERENCE TO RELATED APPLICATIONS

This application is a continuation of U.S. application Ser. No. 15/940,343 filed Mar. 29, 2018, which is a continuation-in-part of U.S. application Ser. No. 15/389,296, filed Dec. 22, 2016, which is a continuation of U.S. application Ser. No. 12/661,042 filed Mar. 10, 2010, now abandoned, which claims the benefit of U.S. Provisional Application No. 61/210,058 filed Mar. 13, 2009, each of which is incorporated by reference in its entirely herein, and for all purposes. U.S. application Ser. No. 12/661,042 is also a continuation-in-part of U.S. application Ser. No. 12/229,207, filed Aug. 20, 2008, now U.S. Pat. No. 8,353,932, which claims the benefit of U.S. Provisional Application No. 60/994,083, filed Sep. 17, 2007, each of which is incorporated by reference in its entirely herein, and for all purposes.

BACKGROUND OF THE INVENTION

The present invention is directed to polyaxial bone screws for use in bone surgery, particularly spinal surgery, and elongate connecting members that are at least somewhat plastically deformable. Such screws have a receiver or head that can swivel about a shank of the bone screw, allowing the receiver to be positioned in any of a number of angular configurations relative to the shank.

Many spinal surgery procedures require securing various implants to bone and especially to vertebrae along the spine. For example, elongate or longitudinal connecting members, such as solid rigid rods are often utilized that extend along the spine to provide support to vertebrae that have been damaged or weakened due to injury or disease. Such elongate members must be supported by certain vertebrae and support other vertebrae.

The most common mechanism for providing vertebral support is to implant bone screws into certain bones which then in turn support the elongate member or are supported by the elongate member. Bone screws of this type may have a fixed head or receiver relative to a shank thereof. In the fixed bone screws, the head cannot be moved relative to the shank and the rod or other elongate member must be favorably positioned in order for it to be placed within the head. This is sometimes very difficult or impossible to do. Therefore, polyaxial bone screws are commonly preferred.

Polyaxial bone screws allow rotation of the receiver about the shank until a desired rotational position of the receiver is achieved relative to the shank. Thereafter, a rod or other elongate connecting member can be inserted into the receiver and eventually the rod and the receiver are locked or fixed in a particular position relative to the shank.

A variety of polyaxial or swivel-head bone screw assemblies are available. One type of bone screw assembly includes an open head or receiver that allows for placement of a rod or other elongate member within the receiver. A closure top or plug is then used to capture the rod in the receiver of the screw. Thus, in such bone screws, the closure top or plug pressing against the rod not only locks the rod in place but also locks the bone screw shank in a desired angular position with respect to the receiver. A draw back to such a system occurs when the rod or other elongate connecting member is made from a material that is more flexible and may be more readily deformed or exhibit creep or viscoelastic behavior. Creep is a term used to describe the tendency of a material to move, flow or to deform permanently to relieve stresses. Material deformation occurs as a result of long term exposure to levels of stress that are below the yield or ultimate strength of the material. Rods and other longitudinal connecting members made from polymers, such as polyetheretherketone (PEEK), have a greater tendency to exhibit creep, than, for example metals or metal alloys. When a rod or other longitudinal connecting member exhibits creep deformation over time, the closure top may no longer tightly engage the connecting member. This in itself is not necessarily problematic. However, such loosening also results in loosening of the frictional engagement between the receiver and the bone screw shank that locks the angular orientation of the shank with respect to the receiver. Body movement and stresses may then result in undesirable pivoting of the shank with respect to the receiver causing mis-alignment, greater stress and further loosening of the various polyaxial bone screw components.

SUMMARY OF THE INVENTION

A polyaxial bone screw assembly of the present invention includes a shank having a generally elongate body with an upper end portion and a lower threaded portion for fixation to a bone. The bone screw assembly further includes a receiver having a top portion and a base. The top portion is open and has a channel. The base includes an inner seating surface partially defining a cavity and has a lower aperture or opening. The channel of the top portion communicates with the cavity, which in turn communicates with an opening to an exterior of the base. The shank upper portion is disposed in the receiver cavity and the shank extends through the receiver base opening. The cooperating shapes of the shank upper portion external surface and the receiver inner surface enable selective angular positioning of the shank body with respect to the receiver. The shank upper surface engages a compression insert that in turn engages a longitudinal connecting member being supported within the receiver. In certain embodiments, the compression insert includes a planar bottom seat and spaced planar sides for closely receiving an elongate connecting member that has planar sides. Such a compression insert can also receive a cylindrical or other shaped connecting member. A single-piece closure structure initially engages the connecting member and, after some plastic deformation of such member, then the closure structure engages the compression insert for securing the assembly in a wide range of angular orientations.

OBJECTS AND ADVANTAGES OF THE INVENTION

Objects of the invention include: providing an implant wherein all of the parts remain together and do not separate; providing a lightweight, low profile polyaxial bone screw that assembles in such a manner that the components cooperate to create an overall structure that prevents unintentional disassembly; providing a polyaxial bone screw that provides substantially independent locking for the bone screw shank and a deformable longitudinal connecting member; providing such an assembly that includes a flexible longitudinal connecting member that may be of non-circular or circular cross-section; providing such an assembly that remains in a locked position even if the flexible longitudinal connecting member undergoes deformation such as creep;

providing a polyaxial bone screw with features that provide adequate frictional or gripping surfaces for bone implantation tools and may be readily, securely fastened to each other and to bone; and providing apparatus and methods that are easy to use and especially adapted for the intended use thereof and wherein the apparatus are comparatively inexpensive to make and suitable for use.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded front elevational view of a medical implant assembly according to the invention including a polyaxial bone screw having a receiver, a bone screw shank, a lower compression insert and a closure structure cooperating with a longitudinal connecting member in the form of a bar of non-circular cross-section.

FIG. 2 is an enlarged upper perspective view of the compression insert of FIG. 1.

FIG. 3 is an enlarged lower perspective view of the compression insert of FIG. 1.

FIG. 4 is an enlarged top plan view of the compression insert of FIG. 1.

FIG. 5 is an enlarged side elevational view of the compression insert of FIG. 1.

FIG. 9 is an enlarged and partial front elevational view of the bone screw shank, receiver, insert and longitudinal connecting member of FIG. 1 shown assembled and further shown with the closure structure of FIG. 1 in an early stage of assembly with the receiver and with portions broken away to show the detail thereof.

FIG. 10 is an enlarged and partial front elevational view of the bone screw shank, receiver, insert and longitudinal connecting member of FIG. 1 shown assembled with the closure structure of FIG. 1 and with portions broken away to show the detail thereof.

DETAILED DESCRIPTION OF THE INVENTION

Figure 6:
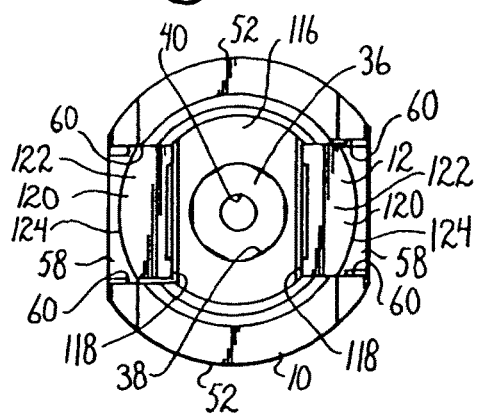
FIG. 6 is an enlarged top plan view of the bone screw shank, receiver and the insert being shown during assembly of the insert into the receiver.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. It is also noted that any reference to the words top, bottom, up and down, and the like, in this application refers to the alignment shown in the various drawings, as well as the normal connotations applied to such devices, and is not intended to restrict positioning of bone attachment assemblies of the application and cooperating connecting members in actual use.

With reference to FIGS. 1-13, the reference number 1 generally represents an embodiment of a medical implant assembly according to the present invention. The assembly 1 includes a polyaxial bone screw 3 having a shank 4 that further includes a threaded body 6 integral with an upper portion 8; a receiver 10; and a lower compression or pressure insert 12. The medical implant assembly 1 further includes a longitudinal connecting member 14 and a closure structure 16. The shank 4, receiver 10, and compression insert 12 are typically factory assembled prior to implantation of the shank body 6 into a vertebra (not shown).

As will be described in greater detail below, the illustrated shank 4 is top loaded into the receiver 10 and thereafter the substantially spherical upper portion 8 slidingly cooperates with an inner substantially spherical inner surface of the receiver 10 such that the receiver 10 and the shank 4 can be secured at any of a plurality of angles, articulations or rotational alignments relative to one another and within a selected range of angles both from side to side and from front to rear, to enable flexible or articulated engagement of the receiver 10 with the shank 4 until both are locked or fixed relative to each other near the end of an implantation procedure. It is noted that although the drawing figures show a top loaded polyaxial mechanism having a spherical sliding connection between the shank upper portion and the receiver inner surface, other kinds of top loaded and bottom loaded embodiments may be utilized according to the invention.

For example, bottom loaded bone screws, such as that disclosed in Applicant's U.S. Pat. Pub. No. 2007/0055244 (U.S. patent application Ser. No. 11/522,503 filed Sep. 14, 2006), the disclosure of which is incorporated by reference herein, having a threaded capture connection between a shank upper portion and a retainer structure disposed within the receiver may be utilized for providing a polyaxial connection between the receiver and the shank for use with the present invention. Specifically, U.S. Pat. Pub. No. 2007/0055244 discloses a bone screw shank that includes an upper portion that further includes an outer helical thread mateable with a retaining structure that includes a mating inner helical thread. The retaining structure has a partially spherical surface that is slidingly mateable with a cooperating inner surface of the receiver, allowing for a wide range of pivotal movement between the shank and the receiver. Bottom or top loaded polyaxial bone screws with other types of capture connections may also be used according to the invention, including but not limited to other types of threaded connections, frictional connections utilizing frusto-conical or polyhedral capture structures, or other integral top or downloadable shanks.

The shank 4, best illustrated in FIGS. 1 and 9, is elongate, with the shank body 6 having a helically wound bone implantable thread 24 extending from near a neck 26 located adjacent to the upper portion 8 to a tip 28 of the body 6 and extending radially outwardly therefrom. During use, the body 6 utilizing the thread 24 for gripping and advancement is implanted into the vertebra (not shown) leading with the tip 28 and driven down into the vertebra with an installation or driving tool, so as to be implanted in the vertebra to near the neck 26. The shank 4 has an elongate axis of rotation generally identified by the reference letter A.

The neck 26 extends axially upwardly from the shank body 6. The neck 26 may be of reduced radius as compared to an adjacent top 32 of the threaded body 6. Further extending axially upwardly from the neck 26 is the shank upper portion 8 that provides a connective or capture apparatus disposed at a distance from the threaded body top 32 and thus at a distance from the vertebra when the body 6 is implanted in the vertebra.

Figure 11:
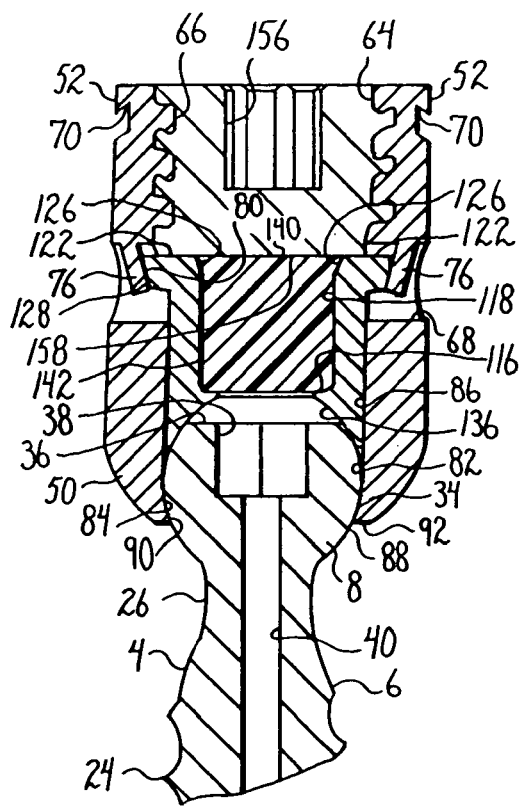
FIG. 11 is an enlarged and partial view similar to FIG. 10 with additional portions broken away to show the detail thereof.

The shank upper portion 8 is configured for a polyaxial connection between the shank 4 and the receiver 10 and capturing the shank 4 upper portion 8 in the receiver 10. The upper portion 8 generally includes an outer spherical surface 34; a planar annular upper surface 36 and with an internal drive feature or structure 38 formed in the surface 36. A driving tool (not shown) has a driving projection configured to fit within the tool engagement structure 38 for both driving and rotating the shank body 6 into the vertebra. As best shown in FIG. 11, the spherical surface 34 is also sized and shaped for sliding contact engagement and ultimate positive frictional mating engagement with the compression insert 12, when the bone screw 3 is assembled, and in any alignment of the shank 4 relative to the receiver 10. The illustrated surface 34 also has approximately the same radius as an inner spherical seating surface (84 described in greater detail below) of the receiver 10, allowing for clearance of the shank 4 with respect to the receiver 10 and thus a desired degree and magnitude of articulation of the shank 4 with respect to the receiver 10. In certain embodiments, the surface 34 is smooth. While not required in accordance with the practice of the invention, the surface 34 may be scored or knurled to further increase frictional positive mating engagement between the surface 34 and the compression insert 12.

The shank 4 shown in the drawings is cannulated, having a small central bore 40 extending an entire length of the shank 4 along the axis A. The bore 40 is defined by an inner cylindrical wall of the shank 4 and has a circular opening at the shank tip 28 and an upper opening communicating with the internal drive 38. The bore 40 is coaxial with the threaded body 6 and the upper portion 8. The bore 40 provides a passage through the shank 4 interior for a length of wire (not shown) inserted into the vertebra (not shown) prior to the insertion of the shank body 6, the wire providing a guide for insertion of the shank body 6 into the vertebra (not shown).

To provide a biologically active interface with the bone, the threaded shank body 6 may be coated, perforated, made porous or otherwise treated. The treatment may include, but is not limited to a plasma spray coating or other type of coating of a metal or, for example, a calcium phosphate; or a roughening, perforation or indentation in the shank surface, such as by sputtering, sand blasting or acid etching, that allows for bony ingrowth or ongrowth. Certain metal coatings act as a scaffold for bone ingrowth. Bio-ceramic calcium phosphate coatings include, but are not limited to: alpha-tri-calcium phosphate and beta-tri-calcium phosphate ($Ca_3(PO_4)_2$), tetra-calcium phosphate ($Ca_4P_2O_9$), amorphous calcium phosphate and hydroxyapatite ($Ca_{10}(PO_4)_6(OH)_2$). Coating with hydroxyapatite, for example, is desirable as hydroxyapatite is chemically similar to bone with respect to mineral content and has been identified as being bioactive and thus not only supportive of bone ingrowth, but actively taking part in bone bonding.

Referring to FIGS. 1 and 6-12, the receiver 10 has a generally squared off U-shaped appearance with a partially cylindrical inner profile and a substantially curved or cylindrical outer profile; however, the outer profile could also be of another configuration, for example, faceted. The receiver has an axis of rotation B that is shown in FIG. 1 as being aligned with and the same as the axis of rotation A of the shank 4, such orientation being desirable during assembly of the receiver 10 with the shank 4 and the insert 12. After such assembly, the bone screw 3 is implanted in a vertebra (not shown). Thereafter, the axis B is typically disposed at an angle with respect to the axis A of the shank 4.

The receiver 10 includes a base 50 integral with a pair of opposed substantially similar or identical upstanding arms 52 forming a squared-off U-shaped cradle and defining a channel 56 between the arms 52 with an upper opening 57 and a lower planar seat 58. The channel 56 is defined in part by planar opposed parallel walls 60 of the receiver arms 52 that run perpendicular to the lower planar seat 58. The walls 60 are spaced to closely receive the bar-shaped connecting member 14 but may also receive a cylindrical rod or oval rod having a diameter or width the same or less than a width of the connecting member 14.

Each of the arms 52 has an interior surface 64 that defines the inner cylindrical profile and includes a partial helically wound guide and advancement structure 66. In the illustrated embodiment, the guide and advancement structure 66 is a partial helically wound interlocking flange form configured to mate under rotation with a similar structure on the closure structure 16, as described more fully below. However, it is foreseen that the guide and advancement structure 66 could alternatively be a square thread, a buttress thread, a reverse angle thread or other thread like or non-thread like helically wound advancement structure for operably guiding under rotation and advancing the closure top downward between the arms 52.

Opposed tool engaging apertures 68 are formed on or through surfaces of the arms 52 that may be used for holding the receiver 10 during assembly with the shank 4 and the retainer structure 12 and also during the implantation of the shank body 6 into a vertebra (not shown). Furthermore, the illustrated embodiment includes upper undercut tool engaging grooves 70 for cooperating with manipulation tools. It is foreseen that tool receiving grooves or apertures may be configured in a variety of shapes and sizes and be disposed at other locations on the receiver arms 52.

A pair of spring tabs 76, each having an upper body portion 78 integral with a respective arm 52, and a lower and inner surface 80 extending below the respective upper body portion 78. The surface 80 is sized and shaped for frictional contact with a portion of the insert 12 as will be described in greater detail below. The tabs 76 are generally directed towards the axis B and downwardly generally toward the base 50. The lower contact surfaces 80 are positioned to engage the compression insert 14 and hold such insert in a desired position, prohibiting rotation of the inert 14 about the axis B. The tabs 76 are typically initially disposed parallel to the axis B and then a tool (not shown) is inserted into the aperture 68 from outside of the receiver 10 to engage and push the respective tab 76, thereby bending the tab 76 inwardly in a direction toward the axis B until the tab 76 is at a desired angular position, such as is illustrated in FIGS. 7-11. Such bending of the tabs 76 may be performed either prior to or after assembly of the receiver 10 with the insert 14. It is also foreseen that the tabs 76 may be machined or otherwise pre-fabricated to be angled or directed toward the axis B so as to engage the insert 14 as shown in the drawing figures. The illustrated tabs 76 are resilient, having a spring-like nature. Thus, when operatively cooperating with the insert 14, the tabs 76 bias against the insert 14, holding such insert in a desired position; and yet the tabs 76 are flexible enough to allow a user to make desired minor adjustments of the position of the insert 14 within the receiver 10.

With further reference to FIGS. 6-11, communicating with and located beneath the channel 56 of the receiver 10 is a chamber or cavity, generally 82, defined in part by an internal substantially spherical seating surface 84 and an inner substantially cylindrical surface 86. The cylindrical surface 86 that defines a portion of the cavity 82 opens upwardly into the channel 56. A closure guide and advancement run-out or recess 87 is disposed between the guide and advancement structure 66 and the cylindrical surface 86. The recess 87 is sized and shaped for receiving a flanged portion of the insert 12 as will be described more fully below. The inner substantially spherical surface 84 that is located below the surface 86 is sized and shaped for mating with the shank upper portion 8. However, it is noted that the surface 84 could have other shapes, for example, conical.

The base 50 further includes a restrictive neck 88 defining a bore, generally 90, communicating with the spherical surface 84 of the cavity 82 and also communicating with a lower exterior 92 of the base 50. The bore 90 is coaxially aligned with respect to the rotational axis B of the receiver 10. The neck 88 and associated bore 90 are sized and shaped to be smaller than an outer radial dimension of the shank upper portion 8, so as to form a restriction at the location of the neck 88 relative to the shank upper portion 8 to prohibit the upper portion 8 from passing through the cavity 82 and out to the lower exterior 92 of the base 50.

With particular reference to FIGS. 2-8, the lower compression or pressure insert 12 includes a substantially cylindrical body 110 integral with a pair of upstanding arms 112. The body 110 and arms 112 form a generally squared-off U-shaped, open, through-channel 114 defined by a planar bottom seating surface 116 and opposed spaced planar walls 118 that are substantially perpendicular to the seating surface 116. The lower seating surface 116 and the walls 118 are sized and shaped to conform to a width of the connecting member 14 and thus configured to operably snugly engage the member 14 at planar outer surfaces thereof as will be described in greater detail below. The arms 112 disposed on either side of the channel 114 each include a top flanged portion 120, each portion 120 including a top planar surface 122, sized and shaped to engage the closure structure 16 and partially cylindrical outer surfaces 124 sized and shaped to fit within the guide and advancement structure run-out relief 87 of the receiver 10. The cylindrical surfaces 124 are disposed substantially perpendicular to the respective adjacent top surfaces 122. Formed in the planar walls 118 near the top surfaces 122 and extending at an oblique angle into the flanged portions 120 are a pair of opposed recesses or relief surfaces 126. As will be described in greater below, the recesses 126 provide relief for material flow of the connecting member 14 material as shown, for example, in FIGS. 11 and 12. Furthermore, each flange 120 includes a bottom surface 127 disposed substantially parallel to the respective top surface 122 and a recessed surface or groove 128 running at an oblique angle with respect to the respective cylindrical surface 124 removing a portion of the flange 120 at the cylindrical surface 124 and the bottom surface 127. The recessed surface or groove 128 is directed downwardly and inwardly toward the channel 114, being spaced from the top surface 122 and intersecting the bottom surface 127. Each of the surfaces 128 is sized and shaped to receive one of the spring tabs 76 of the receiver 10 and engage such respective tab at the inner lower surface 80 thereof. As will be described more fully below, after each of the tabs 76 spring or snap into the respective recessed surface portion 128, the cylindrical surface 124 located on either side thereof prevents rotation of the insert 12 about the axis B with respect to the receiver 10.

Figure 14:
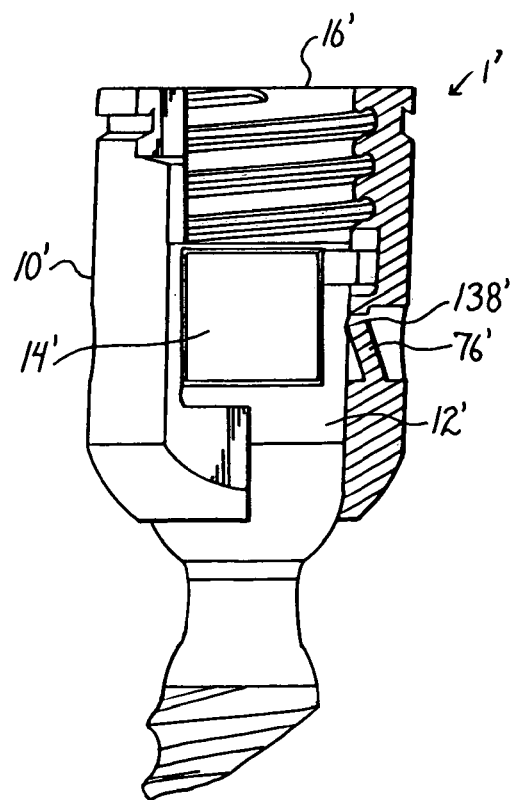
FIG. 14 is an enlarged and partial front elevational view of a second, alternative embodiment of a medical implant assembly according to the invention having a deformable connecting member of rectangular cross-section, with portions broken away to show the detail thereof.

The compression insert 12 further includes a bottom annular surface 130 and a substantially cylindrical outer surface 132. An inner cylindrical surface 134 partially defines a central through-bore extending along a central axis of the compression insert 12. The surface 134 is located between the seating surface 116 and a concave substantially spherical surface 136. The compression insert through-bore is sized and shaped to receive a driving tool (not shown) therethrough that engages the shank drive feature 38 when the shank body 6 is driven into bone. The surface 136 extends between the inner cylindrical surface 134 and the bottom surface 130. The surface 136 is sized and shaped to slidingly and pivotally mate with and ultimately frictionally engage the outer convex spherical surface 34 of the shank upper portion 8. The surface 136 may include a roughening or surface finish to aid in frictional contact between the surface 136 and the surface 34, once a desired angle of articulation of the shank 4 with respect to the receiver 10 is reached. A pair of recesses 138 or flat surfaces are formed in the insert cylindrical surface 132 and located spaced from the flanged portions 120. With reference to FIG. 14, such recesses 138 are sized and shaped to engage spring tabs or other insert holding members as will be described in greater detail below.

Figure 7:
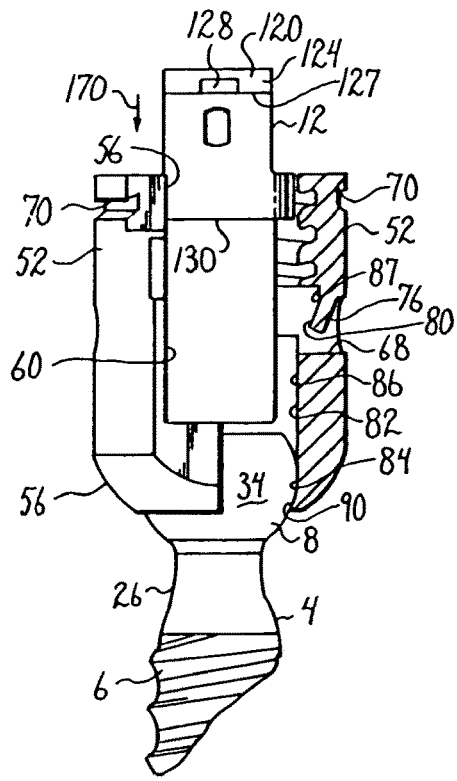
FIG. 7 is an enlarged and partial front elevational view of the bone screw shank, receiver and insert, also showing the insert in a stage of assembly similar to FIG. 6.
Figure 8:
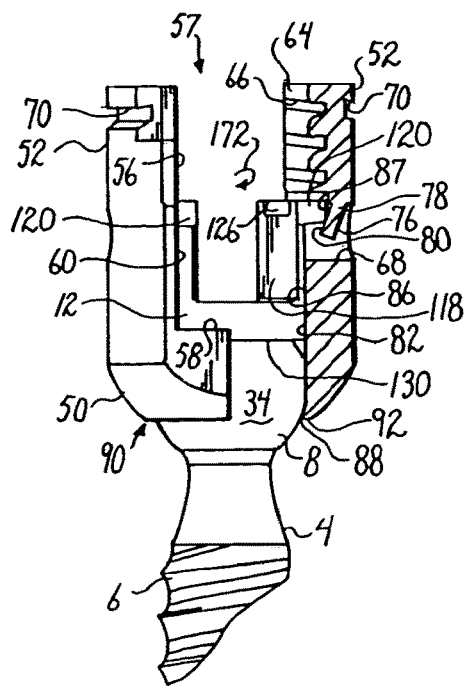
FIG. 8 is an enlarged and partial front elevational view of the bone screw shank, receiver, insert and longitudinal connecting member of FIG. 1 shown assembled and with portions broken away to show the detail thereof.

The cylindrical surface 132 has an outer diameter slightly smaller than a diameter between crests of the guide and advancement structure 66 of the receiver 10 allowing for top loading of the compression insert 12 with the flanged portions 120 being located between the planar walls 60 during insertion of the insert 12 into the receiver 10 as shown in FIGS. 6 and 7. The receiver is then rotated into place as shown in FIG. 8 with the flanged portions 120 being received in the guide and advancement structure run-out or recess 87. As the insert 12 is rotated into a desired position, the spring tabs 76 snap into the recessed portions 124, and thereafter hold the insert 12 in a desired alignment between the channel 56 of the receiver and the channel 114 of the insert 12. The lower compression insert 12 is sized such that the insert 12 is ultimately received within the cylindrical surface 86 of the receiver 10 below the guide and advancement structure 66 with the flanged top portions 120 received in the recesses 87 formed below the guide and advancement structure 66 and the bottom-surface 130 being spaced from the receiver base. The receiver 10 fully receives the lower compression insert 12 and blocks the structure 12 from spreading or splaying in any direction. It is noted that assembly of the shank 4 within the receiver 10, followed by insertion of the lower compression insert 12 into the receiver 10 are assembly steps typically performed at the factory, advantageously providing a surgeon with a polyaxial bone screw with the lower insert firmly snapped into place and thus ready for insertion into a vertebra.

The compression or pressure insert 14 ultimately seats on the shank upper portion 8 and is disposed substantially in the upper cylindrical portion 86 of the cavity 82, with the tabs 76 engaging the insert 14 at the grooves 128, thereby holding the insert 14 in desired alignment with respect to the connecting member 14. In operation, the insert 14 extends at least partially into the channel 56 such that the seating surface 116 substantially contacts and engages the adjacent planar surface of the connecting member 14 when such member 14 is placed in the receiver 10 and the closure structure or top 18 is tightened therein. The connecting member 14 is held in spaced relation with the lower seat 58 of the receiver 10.

With reference to FIGS. 1 and 10-13, the elongate connecting member 14 illustrated in the drawing figures is a solid elongate bar of rectangular cross-section. More particularly, the illustrated embodiment is solid and has as square cross-section. Thus, the member 14 includes a first pair of opposed planar surfaces 140 and a second pair of equally spaced opposed planar surfaces 142 disposed perpendicular to the surfaces 140. The illustrated member 14 further includes beveled edges and first and second end surfaces 144 and 146. The illustrated connecting member 14 is made from a polymer, in particular, polyetheretherketone (PEEK). The member 14 may be made from a variety of materials including metal, metal alloys or other suitable materials, including, but not limited to plastic polymers such as PEEK, ultra-high-molecular weight-polyethylene (UHMWP), polyurethanes and composites, including composites containing carbon fiber. Furthermore, the connecting member 14 may be a component of a dynamic stabilization connecting member, with the bar or bar portion 14 that is operatively disposed within the insert channel 114 also being integral with or otherwise fixed to a more flexible, bendable or damping component that extends between adjacent pairs of bone screws 3. It is foreseen that as long as the longitudinal connecting member has sufficient viscoelastic behavior, any cross-sectional shape (i.e., square, oval, round, non-round) could be used for the longitudinal connecting member. The channel in the insert could be modified to fit the shape of the longitudinal connecting member. After sufficient pressure is applied to the longitudinal connecting member by the one-piece closure, and plastic deformation occurs, additional pressure by the closure is then directly applied to the compression or pressure insert, thereby securely locking both the longitudinal connecting member and the polyaxial mechanism of the bone anchor.

With reference to FIGS. 1 and 9-11, the closure structure or closure top 16 can be any of a variety of different types of closure structures for use in conjunction with the present invention with suitable mating structure on the upstanding arms 52. In the embodiment shown, the closure top 16 is rotatably received between the spaced arms 52. The illustrated closure structure 16 is substantially cylindrical and includes an outer helically wound guide and advancement structure 152 in the form of a flange form that operably joins with the guide and advancement structure 66 disposed on the arms 52 of the receiver 10. The flange form utilized in accordance with the present invention may take a variety of forms, including those described in Applicant's U.S. Pat. No. 6,726,689, which is incorporated herein by reference. It is also foreseen that according to the invention the closure structure guide and advancement structure could alternatively be a buttress thread, a square thread, a reverse angle thread or other thread like or non-thread like helically wound advancement structure for operably guiding under rotation and advancing the closure structure 16 downward between the arms 52 and having such a nature as to resist splaying of the arms 52 when the closure structure 16 is advanced into the channel 56. The illustrated closure structure 16 also includes a top surface 154 with an internal drive 156 in the form of an aperture that is illustrated as a hex drive, but may be, for example, a star-shaped internal drive, such as those sold under the trademark TORX or other internal drives, including, but not limited to slotted, tri-wing, spanner, two or more apertures of various shapes, and the like. A driving tool (not shown) sized and shaped for engagement with the internal drive 156 is used for both rotatable engagement and, if needed, disengagement of the closure 16 from the receiver arms 52. It is also foreseen that the closure structure 15 may alternatively include a break-off head designed to allow such a head to break from a base of the closure at a preselected torque, for example, 70 to 140 inch pounds. Such a closure structure would also include a base having an internal drive to be used for closure removal. A bottom surface 158 of the closure is planar, but may include a point, points, a rim or roughening for engagement with the surface 140 of the bar-like connecting member 14. The bottom surface 158 is sized and shaped for engagement with both the connecting member surface 140 and the top planar surfaces 122 of the flanged portions 120 of the insert 12. As will be described in greater detail below, during assembly, the surface 158 first engages the surface 140 of the connecting member. Then, as the closure member 16 is rotated, the surface 158 presses against the surfaces 120, pushing the insert 16 downwardly onto the shank upper portion 8 that in turn presses against the receiver surface 84, locking the shank 4 with respect to the receiver 10 in a desired angular or articulated position. With time, the connecting member 14 may undergo creep or other plastic deformation that may lessen the engagement between the surfaces 140 and 158. However, regardless of any movement of the surface 140, the frictional engagement between the closure member 16 and the insert 12, both preferably made from a metal or metal alloy, such as stainless steel or titanium, will remain rigid and secure.

The closure top 16 may further include a cannulation through bore extending along a central axis thereof and through a surface of the drive 156 and the bottom surface 158. Such a through bore provides a passage through the closure 16 interior for a length of wire (not shown) inserted therein to provide a guide for insertion of the closure top into the receiver arms 52.

With particular reference to FIG. 1, prior to the polyaxial bone screw 3 being placed in use according to the invention, the tip 28 of the shank 6 is inserted into the receiver 10 at the upper opening 57 and then through the bore 88 to a position wherein the shank upper portion 8 is seated on the inner surface 84 of the receiver. Then, with particular reference to FIGS. 6-7, the insert 12 is inserted into the opening 57 with the flanged portions 120 aligned in the channel 56, each flanged portion 120 being located between a pair of opposed planar walls 60 partially defining the channel 56. The insert 12 is then moved downwardly in the channel 56 and toward the cavity 82 as illustrated by the arrow 170 in FIG. 7. As the insert 12 is moved downwardly into the cylindrical portion 86 of the cavity 82, the spring tabs 76 may be pushed outwardly away from the axis A by the flanged portions 120. Once the flanged portions 120 are located below the guide and advancement structure 66 and adjacent the run-out relief 87, the insert 12 is rotated about the axis B of the receiver 10 as illustrated by the arrow 172 in FIG. 8. The flanged portions 120 fit within the relief 87. Once each flanged portion 120 is located centrally with a respective arm 52 of the receiver 10, rotation is ceased and the spring tabs 76 slide or snap into the grooves 128. A slight downward movement of the insert 12 may be needed to fully engage the spring tabs 76 in the grooves with each of the surfaces 80 being biased against the respective groove surfaces 128. The insert 12 is now locked into place inside the receiver 10 with the guide and advancement structure 66 prohibiting upward movement of the insert out of the opening 57 and the spring tabs 76 that are biasing against the insert 12 at the grooves 128 prohibiting rotational movement of the insert 12 with respect to the receiver 10 about the receiver axis B. As illustrated in FIG. 10, the insert 12 seats on the shank upper portion 8 with the surface 136 in sliding engagement with the surface 34. The run-out or relief 87 is sized and shaped to allow for some upward and downward movement of the insert 12 toward and away from the shank upper portion 8 such that the shank 8 is freely pivotable with respect to the receiver 10 until the closure structure 16 presses on the insert 12 that in turn presses upon the upper portion 8 into locking frictional engagement with the receiver 10 at the surface 84.

In use, the bone screw 3 is typically screwed into a bone, such as a vertebra (not shown), by rotation of the shank 4 using a driving tool (not shown) that operably drives and rotates the shank 4 by engagement thereof with the tool engagement structure 38. The vertebra (not shown) may be pre-drilled to minimize stressing the bone and have a guide wire (not shown) that is shaped for the cannula 40 inserted to provide a guide for the placement and angle of the shank 4 with respect to the vertebra. A further tap hole may be made using a tap with the guide wire as a guide. Then, the bone screw 3 is threaded onto the guide wire utilizing the cannulation bore 40 by first threading the wire into the bottom opening 28 and then out of the top at the internal drive 38. The shank 4 is then driven into the vertebra, using the wire as a placement guide.

With reference to FIGS. 10-11, the connecting member 14 is eventually positioned in an open or percutaneous manner within the receiver channel 56 and then into the channel 114 defined by the bottom planar seating surface 116 and the planar walls 118. The member surfaces 140 and 142 are closely received within the planar walls of the insert 12. The closure structure or top 16 is then inserted into and advanced between the arms 52 so as to bias or push against the upper surface 140 of the connecting member 14. Alignment of the planar surfaces 140 and 142 of the connecting member 14 with the squared off U-shaped channel 114 of the insert 14 is initially provided and then maintained by pressure placed on the insert 12 at grooves 128 by the spring tabs 76. The closure structure 16 is rotated, using a tool engaged with the inner drive 156 until a selected pressure is reached at which point the connecting member 14 fully engages the planar surfaces 116 and 118 of the insert 12 and the connecting member 14 is urged toward, but not in contact with the lower seat 58 of the receiver 10 that defines the squared off U-shaped channel 56. As the closure member 16 is rotated and urged downwardly against first the connecting member 14 and then the flanged portions 120 of the insert 12, for example, with a pressure of about 80 to about 120 inch pounds, frictional locking of the shank upper portion 8 against the receiver surface 84 at a desired angle of articulation is accomplished not only by forces transferred through the connecting member 14 but also by direct engagement between the closure member 16 and the insert 12 at the flanged portions 120. Thus, if the connecting member 14 exhibits creep, as would be expected by the PEEK connecting member 14 illustrated in the drawing figures, movement or flow of the member 14 would not diminish the locking frictional engagement between the shank upper portion 8 and the receiver surface 84 as neither the insert 12 nor the receiver 10 (both made from metal such as titanium, for example) would exhibit creep or other deformation. In such an assembly 1, the benefit to the patient of a flexible or dynamic connecting member 14 as well as the benefit of a bone screw 3 having a secure locking mechanism (metal to metal frictional engagement) is accomplished.

If removal of the connecting member 14 from any of the bone screws 3 is necessary, or if it is desired to release the connecting member 14 at a particular location, disassembly is accomplished by using the driving tool (not shown) that mates with the internal drive 156 on the closure structure 16 to rotate and remove the closure structure 16 from the cooperating receiver 10. Disassembly is then accomplished in reverse order to the procedure described previously herein for assembly.

Figure 12:
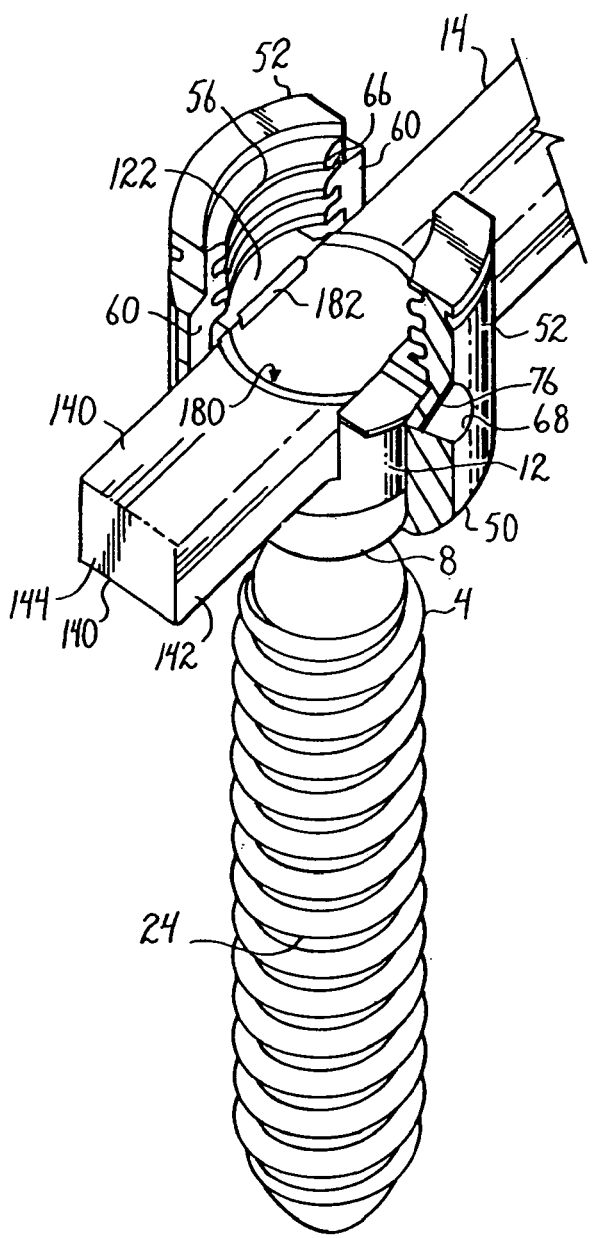
FIG. 12 is an enlarged and partial upper perspective view of the assembly of FIG. 10 but with the closure structure removed to show deformation of the longitudinal connecting member and also shown with other portions broken away to show the detail thereof.

With reference to FIG. 12, there is illustrated an assembly 1 of the invention wherein the closure member 16 has been removed after an amount of time wherein the PEEK connecting member 14 has exhibited some deformation due to creep. It is noted how the member 14 is compressed at the area 180 where the closure structure 16 bottom surface 158 had been pressing on the member upper surface 140. Also illustrated is the flow of connecting member 14 material 182 into the recesses 126 formed in the insert 12. Such material 182 disposed within the recesses 126 advantageously provides further frictional engagement between the insert 12 and the connecting member 14.

Figure 13:
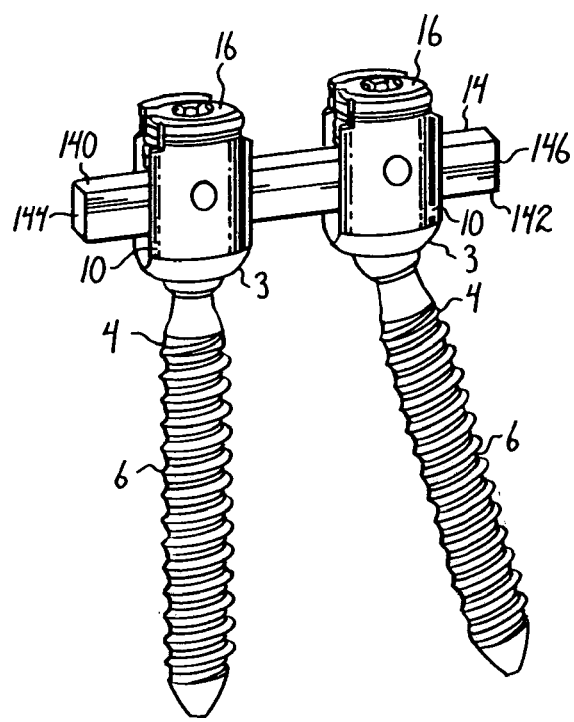
FIG. 13 is a perspective view showing the assembly of FIG. 1 attached to a second polyaxial bone screw of FIG. 1.

With reference to FIG. 13, the connecting member 14 is typically assembled with two or more bone screws 3. The combination of the connecting member 14 with planar surfaces and the bone screw receiver 10 having a channel and insert 12 that includes planar surfaces for closely receiving the member 14 is shown. An advantage of such an assembly is torsional control of the medical implant system. As compared to rigid rods made from metals or metal alloys, a dynamic medical implant 1 of the invention is desirably more flexible in bending or flexing. Furthermore, the combination between a bar-shaped connecting member and receiver with planar surfaces provides stability and strength to withstand torsional forces that, for example, a cylindrical PEEK rod captured by a receiver with a U-shaped channel would not provide. If a more rigid support is eventually required, the bar-shaped member 14 may be replaced by a stiffer cylindrical or bar-shaped rod having a diameter or width the same or similar to the cross-sectional width of the member 14. Such a rod of circular cross-section would be adequately received and closely held between the planar walls 116 and 118 of the insert 14 and the same or similar closure top 16 could be used to hold such a rod in the receiver 10 and also lock the polyaxial mechanism, placing the shank 4 and the receiver 10 in a desired angular relationship with one another.

Figure 15:
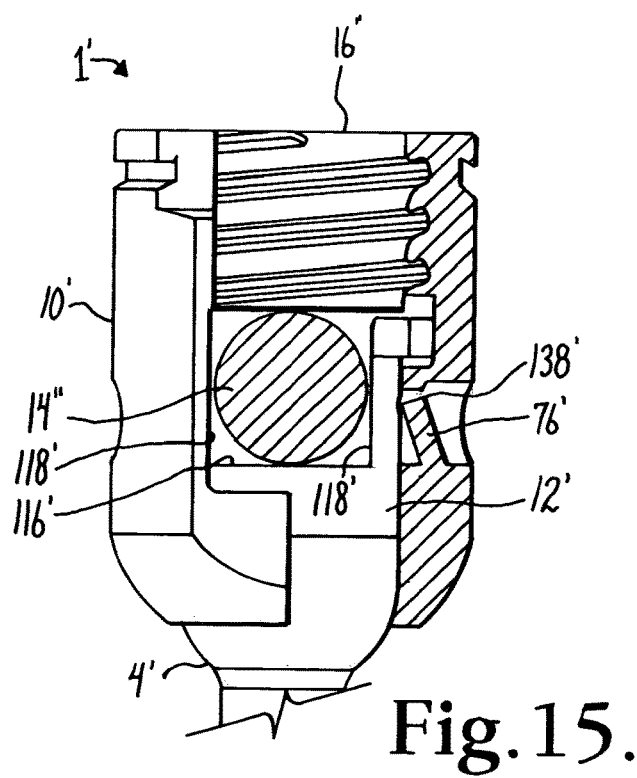
FIG. 15 is an enlarged and partial front elevational view of the embodiment of FIG. 14 with portions broken away to show the detail thereof and further showing replacement of the deformable connecting member with a rigid rod of circular cross-section.

With reference to FIGS. 14 and 15, an alternative assembly 1' is illustrated. The assembly 1' is identical to the assembly 1 previously described herein with the exception of an aspect of a receiver 10' that is otherwise substantially similar to the receiver 10 previously described herein. The assembly 1' therefore includes a shank 4', an insert 12', a connecting member 14' and a closure member 16' that are identical or substantially similar in form and function to the respective shank 4, insert 12, connecting member 14 and closure member 16 previously described herein with respect to the assembly 1. As compared to the spring tabs 76 of the receiver 10 that extend in a downward direction toward the base 50 of the receiver 10, the receiver 10' includes a pair of spring tabs 76' that extend upwardly and toward a closure structure 16'. The spring tabs 76' bias against the insert 12' at recesses 138' identical to the recesses 138 described herein with respect to the insert 12.

With reference to FIG. 15, if a more rigid support is eventually required, the bar-shaped member 14' is shown being replaced by a stiffer cylindrical rod 14" having a diameter equal to the width of the member 14'. As shown in FIG. 15, the rod 14" is received and closely held between planar walls 116' and 118' of the insert 14' and a closure top 16" substantially similar to the closure top 16' abuts against the rod 14" but does not abut against the lower pressure insert 12'. Frictional engagement of the closure top 16" and the rod 14" fixes the rod 14" in the receiver 10' and also locks the polyaxial mechanism, fixedly placing the shank 4' and the receiver 10' in a desired angular relationship with one another.

Figure 16:
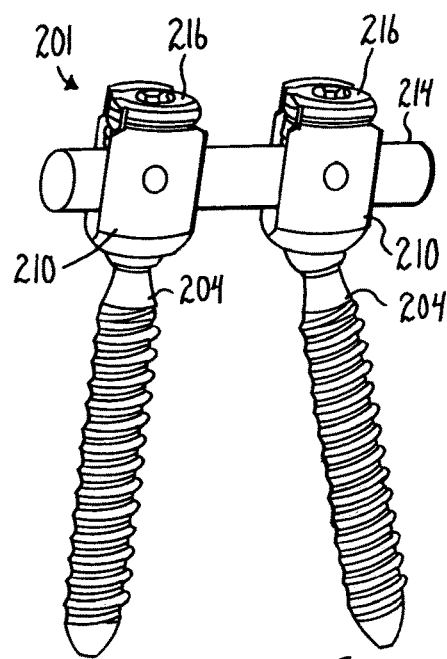
FIG. 16 is a perspective view showing two bone screws of a third, alternative embodiment of a medical implant assembly according to the invention holding a deformable connecting member of circular cross-section.
Figure 17:
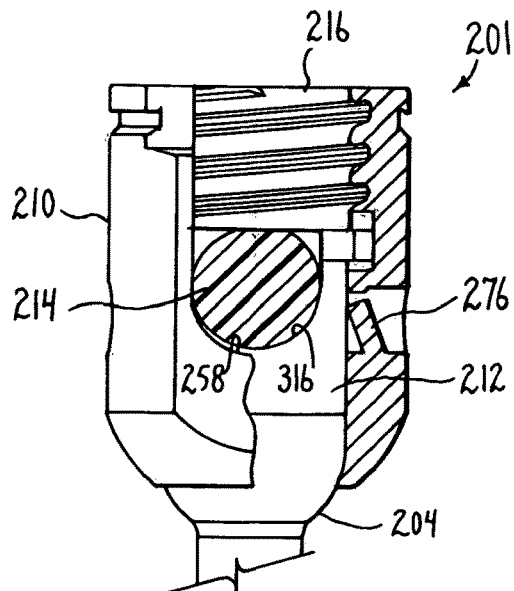
FIG. 17 is an enlarged and partial front elevational view of one of the bone screws and the connecting member of FIG. 16 with portions broken away to show the detail thereof.
Figure 18:
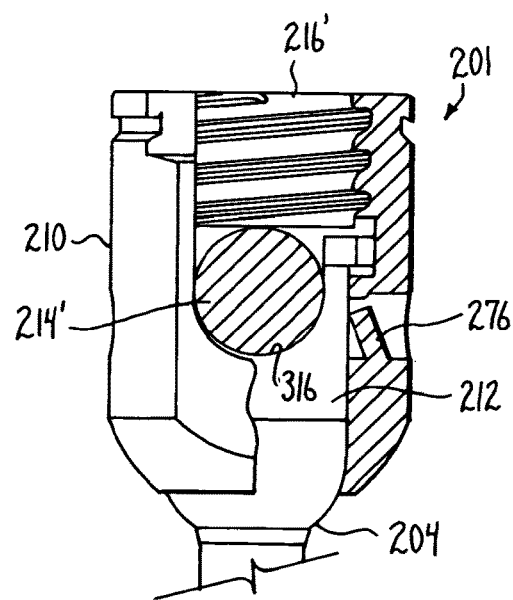
FIG. 18 is an enlarged and partial front elevational view of the embodiment of FIG. 17 with portions broken away to show the detail thereof and further showing replacement of the deformable connecting member with a rigid rod of circular cross-section.

With reference to FIGS. 16-18, another alternative assembly 201 is illustrated. The assembly 201 is identical to the assembly 1' previously described herein with the exception that the bottom planar surfaces of the lower pressure insert and receiver have been replaced by curved surfaces, forming U-shaped channels for holding a connecting member having substantially circular cross-section, such as deformable or rigid rods. The assembly 201 therefore includes a shank 204, a receiver 210, an insert 212, a connecting member 214 and a closure member 216 that are substantially similar in form and function to the respective shank 4, receiver 10, insert 12, connecting member 14 and closure member 16 previously described herein with respect to the assembly 1 with the following exceptions: The receiver 210 includes spring tabs 276 that are identical or substantially similar to the spring tabs 76' of the assembly 1'. Also, a U-shaped surface 258 replaces the planar surface 58 that partially defines the channel 56 of the receiver 10. Similarly, the insert 212 includes a U-shaped surface 316 that replaces the planar bottom surface 116 and portions of the side surfaces 118 of the insert 12. Therefore, the insert 212 and the receiver 210 are sized and shaped to closely receive the connecting member 214 that differs from the connecting member 14 in that the member 214 has a circular cross-section as compared to the rectangular cross-section of the member 14. As best illustrated in FIG. 17, the rod-shaped deformable connecting member 214 is closely held or cradled by the insert 212 surface 316; with the connecting member 214 being held spaced from the receiver surface 258. The closure top 216 presses and deforms the connecting member 214 and also engages the lower pressure insert 212. Engagement between the closure 216 and the insert 212 keeps the bone screw shank 204 in a desired locked position with respect to the receiver 210 even if further deformation of the connecting member 214 occurs that might loosen the connection between the connecting member 214 and the closure top 216.

With reference to FIG. 18, if a more rigid support is eventually required, the deformable rod 214 is shown being replaced by a stiffer cylindrical rod 214'. The more rigid rod 214' is received and closely held by the surface 316 and a closure top 216' substantially similar to the closure top 216 abuts against the rod 214' but does not abut against the lower pressure insert 212. Frictional engagement of the closure top 216' and the rod 214' fixes the rod 214' in the receiver 210 and also locks the polyaxial mechanism, fixedly placing the shank 204 and the receiver 210 in a desired angular relationship with one another.

It is to be understood that while certain forms of the present invention have been illustrated and described herein, it is not to be limited to the specific forms or arrangement of parts described and shown.

What is claimed is:

1. A pivotal bone anchor assembly for securing an elongate rod to a bone via a closure top, the pivotal bone anchor assembly comprising:
   a receiver having a longitudinal axis, a base, and an integral upper portion defining a channel extending transverse to the longitudinal axis configured to receive the elongate rod, the base including a cavity in communication with a bottom surface of the base through a bottom opening and having a spherical seating surface proximate the bottom opening, the receiver including an axial bore centered about the longitudinal axis and extending from the bottom opening to a top of the integral upper portion, the axial bore defined in part by the bottom opening, an inner cylindrical surface in the cavity, and an at least partially cylindrical inner surface in the channel having a discontinuous helically wound thread formed therein, the axial bore including a structure with a downwardly-facing surface positioned beneath the discontinuous helically wound thread;
   a shank having a proximal at least partially spherical shaped head and an integral anchor portion extending distally from the head for fixation to the bone, the head being positionable within the receiver cavity with the anchor portion extending downwardly through the bottom opening, the head including an internal drive structure;
   a pressure insert having a longitudinal axis and an upwardly-facing seating surface configured to receive at least an underside portion of the elongate rod, a central opening for a tool to pass through to engage the shank head internal drive structure, a lower surface configured to directly engage the shank head to apply downward pressure thereto, and at least one structure with an upwardly-facing planar surface perpendicular to the insert longitudinal axis and positioned radially outward from the seating surface, the pressure insert being installed into a first position within the receiver channel, wherein upon rotation of the pressure insert about the receiver longitudinal axis into a second position within the receiver channel, the insert at least one structure with the upwardly-facing planar surface is rotated under the receiver downwardly-facing surface so as to inhibit upward movement of the pressure insert within the receiver channel along the receiver longitudinal axis.

2. The pivotal bone anchor assembly of claim 1, wherein at least one receiver inwardly-protruding integral structure is formed into the receiver channel to engage the pressure insert after rotation into the second position so as to inhibit further rotation of the pressure insert in the receiver channel.

3. The pivotal bone anchor assembly of claim 2, wherein the at least one receiver inwardly-protruding integral structure further comprises a pair of opposed inwardly-protruding integral structures formed into opposite sides of the receiver channel.

4. The pivotal bone anchor assembly of claim 2, wherein the at least one receiver inwardly-protruding integral structure further comprises a resilient spring tab.

5. The pivotal bone anchor assembly of claim 1, wherein the insert at least one structure with the upwardly-facing planar surface positioned radially outward from the insert seating surface is disposed in the second position so that the at least one upwardly-facing planar surface is entirely below a top side surface of the rod positioned on the insert seating surface.

6. The pivotal bone anchor assembly of claim 1, wherein the insert seating surface is further defined and flanked by a pair of upright arms.

7. The pivotal bone anchor assembly of claim 6, wherein each of the insert upright arms has a top surface defining an upwardly-facing planar surface perpendicular to the insert longitudinal axis when the pressure insert is installed within the receiver channel.

8. The pivotal bone anchor assembly of claim 1, wherein the pressure insert has a top surface that is spaced apart from a bottom surface of the closure top when the closure top is fully engaged with the receiver channel helically wound thread to secure the elongate rod within the channel of the receiver.

9. The pivotal bone anchor assembly of claim 1, wherein the pressure insert further comprises a pair of oppositely spaced flanges projecting radially outward, each flange having a top surface defining an upwardly-facing planar surface and extending, upon rotation of the pressure insert into the second position, under the receiver downwardly-facing surface configured to at least partially overlap and be engageable with the flange upwardly-facing planar surface.

10. The pivotal bone anchor assembly of claim 1, wherein the insert central opening is configured to allow the tool to pass therethrough so that the tool engages the internal drive structure formed on the shank head when the shank is co-axially aligned with the receiver longitudinal axis.

11. The pivotal bone anchor assembly of claim 1, wherein the pressure insert is top loaded into the receiver channel when installed in the first position.

12. The pivotal bone anchor assembly of claim 1, wherein the pressure insert further comprises oppositely spaced apart notches that are configured, upon rotation of the pressure insert into the second position, to engage opposed integral structures protruding inwardly toward the receiver longitudinal axis to prevent the further rotation of the pressure insert within the receiver channel.

13. The pivotal bone anchor assembly of claim 12, wherein the notches are located on the insert adjacent the insert at least one radially outward upwardly-facing planar surface.

14. The pivotal bone anchor assembly of claim 1, wherein the insert lower surface further comprises a downwardly-facing spherical surface.

15. The pivotal bone anchor assembly of claim 1, wherein the shank head is installed into the receiver cavity prior to the pressure insert being installed into the receiver channel.

16. The pivotal bone anchor assembly of claim 1, wherein the shank head includes a spherical outer surface slidably engageable with the receiver cavity spherical seating surface.

17. The pivotal bone anchor assembly of claim 1, wherein the shank is cannulated along an entire length thereof.

18. The pivotal bone anchor assembly of claim 1, wherein the receiver channel helically wound thread comprises a discontinuous flange form.

19. The pivotal bone anchor assembly of claim 1, wherein the receiver helically wound thread comprises one of a discontinuous square thread, buttress thread, or reverse angle thread.

20. The pivotal bone anchor assembly of claim 1, wherein a separate retainer is positioned in the receiver cavity so as to be in pivotal engagement with the cavity spherical seating surface, the retainer configured to hold the shank in the receiver.

21. A pivotal bone anchor assembly for securing an elongate rod to a bone via a closure top, the bone anchor assembly comprising:

a receiver having a longitudinal axis, a base, and a pair of upstanding arms extending upwardly from the base with opposed inner surfaces defining an upwardly-opening rod-receiving channel extending through outwardly-facing front side and back side surfaces of the receiver and configured to receive the elongate rod, the arm inner surfaces having a closure top mating feature formed thereon, the base including a cavity in communication with the rod-receiving channel and with a bottom surface of the base through a bottom opening, the receiver including an axial bore centered about the longitudinal axis and extending from the bottom opening to a top of the upstanding arms, the axial bore defined in part by the bottom opening, an inner cylindrical surface in the cavity, and an at least partially cylindrical inner surface in the channel having a discontinuous helically wound thread formed therein, the axial bore including at least one downwardly-facing surface formed in an interior surface thereof and a pair of opposed integral structures facing inwardly toward the longitudinal axis between the closure top mating feature and the cavity, the cavity having a spherical seating surface proximate the bottom opening;

a shank having a longitudinal axis and a proximal capture portion with a spherical outer surface on a spherically shaped head and an anchor portion extending distally from the capture portion for fixation to the bone, the shank capture portion being positionable within the receiver cavity with the shank anchor portion extending downwardly through the bottom opening, the spherically shaped head having a central internal driving structure formed around the shank longitudinal axis and centered thereon; and a pressure insert having an upper seating surface configured to receive at least an underside portion of the elongate rod, at least one upwardly-facing surface positioned radially outward from the insert seating surface, a central opening for a tool to pass through so as to be engageable with the internal driving structure formed in the shank head, a lower surface configured to engage the shank capture portion spherical outer surface, and an outer side surface having diametrically opposite notches formed therein, the pressure insert being top loaded within the receiver axial bore into a first position within the receiver axial bore with the insert seating surface in a non-alignment orientation with respect to the receiver rod-receiving channel, wherein upon rotation of the pressure insert about the receiver longitudinal axis into a second position within the receiver axial bore, with the insert seating surface in a co-linear alignment with the receiver rod-receiving channel, the at least one insert upwardly-facing surface is configured to be positioned under the receiver axial bore downwardly-facing surface so as to inhibit the pressure insert from moving back up within the receiver axial bore, and the insert outer side surface diametrically opposed notches are configured to accept the receiver inwardly facing integral structures so as to prevent further rotation of the pressure insert within the receiver axial bore.

22. The pivotal bone anchor assembly of claim 21, wherein the receiver inwardly facing integral structures are formed into the receiver axial bore prior to top loading the pressure insert into the receiver axial bore.

23. The pivotal bone anchor assembly of claim 21, wherein the receiver inwardly facing integral structures further comprise a pair of opposed non-cylindrically shaped inwardly-protruding integral structures formed into opposite sides of the receiver axial bore.

24. The pivotal bone anchor assembly of claim 21, wherein the receiver inwardly facing integral structures further comprise resilient spring tabs.

25. The pivotal bone anchor assembly of claim 21, wherein the receiver closure top mating feature further comprises a discontinuous helically-wound guide and advancement structure.

26. The bone pivotal anchor assembly of claim 25, wherein the discontinuous helically-wound guide and advancement structure is one of a flange form, square thread, buttress thread, or reverse angle thread.

* * * * *